United States Patent [19]

Meyer

[11] 3,983,151

[45] Sept. 28, 1976

[54] PROCESS FOR THE PREPARATION OF 4-HYDROXY-3-METHOXY-PHENYLACETONITRILE

[75] Inventor: Horst Meyer, Wuppertal, Germany

[73] Assignee: Bayer Aktiengesellschaft, Germany

[22] Filed: Nov. 21, 1975

[21] Appl. No.: 634,126

[30] Foreign Application Priority Data
Dec. 3, 1974 Germany............................. 2457079

[52] U.S. Cl.......................... 260/465 F; 260/471 R
[51] Int. Cl.$^2$......................................... C07C 121/75
[58] Field of Search................................ 260/465 F

[56] References Cited
OTHER PUBLICATIONS

Short et al., Tetrahedron, vol. 29, pp. 1931–1939, (1973).

Primary Examiner—Lewis Gotts
Assistant Examiner—Dolph H. Torrence

[57] ABSTRACT

3-Methoxy-4-hydroxyphenylacetonitrile, which is a known chemical intermediate, is obtained from the reaction of an N-(lower alkyl) 3-methoxy-4-hydroxybenzylamine with hydrogen cyanide.

10 Claims, No Drawings

PROCESS FOR THE PREPARATION OF 4-HYDROXY-3-METHOXY-PHENYLACETONITRILE

The present invention relates to a new process for the preparation of 4-hydroxy-3-methoxy-phenylacetonitrile which is an intermediate for the preparation of pharmaceuticals.

4-Hydroxy-3-methoxyphenylacetonitrile has, like all other hydroxyphenylacetonitriles, hitherto only been accessible with difficulty, since the usual nitrile synthesis via the benzyl halide requires prior protection of the phenolic hydroxy group. Thus, homovanillic acid (3-methoxy-4-hydroxyphenylacetic acid) has been prepared, starting from vanillin, by the following multi-stage method:

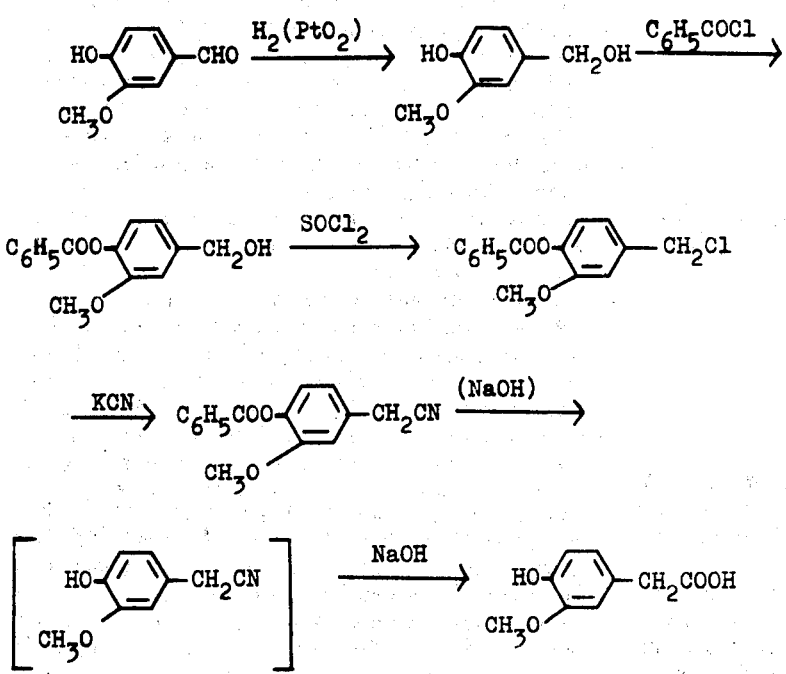

(See, e.g., Berlin, Scherlin and Serebrennikowa, Z. Obsc. chim. 19, 759, 766 (1949) C.A. 1950, 1,058).

Other methods of synthesis of homovanillic acid utilizing acylated 4-hydroxy-3-methoxyacetonitrile as an intermediate, are even more expensive (see, e.g. Hahn and Schales, Ber. 67, 1,486 (1934) and E. H. Fisher and H. Hibbert JACS 69, 1,208 (1947)).

In a more recent publication, these expensive routes are avoided by first subjecting vanillin to reductive amination with methylamine and then treating the resultant N-methylvanillylamine, in dimethylformamide, with potassium cyanide at temperatures of 110°–130°C:

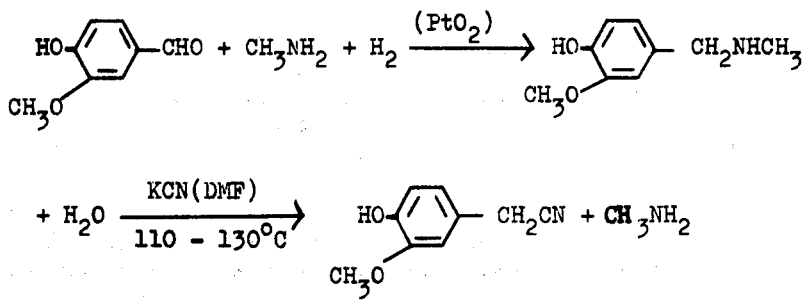

(See, e.g. J. H. Short, D. A. Dunnigan and C. W. Ours, Tetrahedron 29, 1,931 (1973)).

In the Short et al. method one mol of the amine component is heated with 1.1 mols of potassium cyanide in dimethylformamide for 6 hours at 110°–130°C, 0.875 mol of glacial acetic acid are then added and the solvent is removed in vacuo. For the conversion of N-methylvanillylamine to 4-nydroxy-3-methoxy-phenylacetonitrile, a yield of only 58% of theory was reported, which is entirely unsatisfactory for industrial application. These workers postulate the initial intermediate formation of a quinomethide, which undergoes reaction with potassium cyanide:

If N-methyl-4-hydroxy-3-methoxybenzylamine and hydrocyanic acid are used as starting materials, the

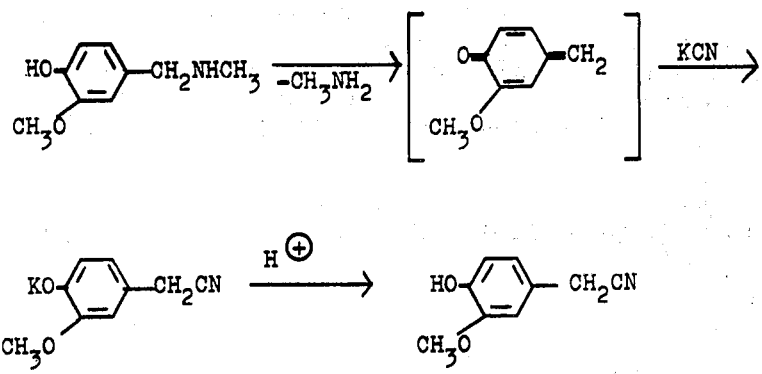

The present invention pertains to a process for the preparation of 3-methoxy-4-hydroxyphenylacetonitrile course of the reaction can be represented by the following equation:

which comprises allowing an N-(lower alkyl)-3-methoxy-4-hydroxybenzylamine to react with hydrogen cyanide in a diluent at temperatures of from about 100°C to about 190°C.

4-Hydroxy-3-methoxyphenylacetonitrile can be graphically depicted as follows:

(I) 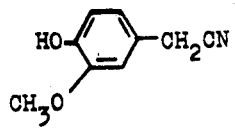

This is thus obtained, in excellent yield and high purity, when an N-(lower alkyl)-vanillylamine of the formula:

(II) 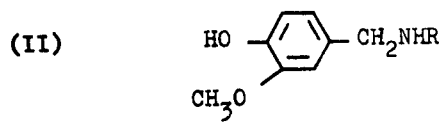

in which
  R represents a lower alkyl radical
is allowed to react with hydrogen cyanide (alternatively known as hydrocyanic acid) at temperatures between 100° and 190°C, preferably at 110°–140°C, in a diluent such as water or an inert organic solvent.

It is distinctly surprising that 4-hydroxy-3-methoxyphenylacetonitrile can be obtained in such good yields and such high purity, with a greatly reduced reaction time, in a single step since from the state of the art, it would not be expected that hydrogen cyanide would be advantageous as compared with alkali metal cyanides.

According to the present invention, it is thus possible to reduce the reaction time from 6 to 2 hours, which is of course economically attractive. More significantly, it is possible to increase the yield to about 90% (88–94%). Finally, the product is obtained in particularly high purity without the need for elaborate purification as by distillation.

The benzylamines of Formula II are known or can be prepared according to known methods and include: (4-hydroxy-3-methoxybenzyl)-methylamine, (4-hydroxy-3-methoxybenzyl)-ethylamine, (4-hydroxy-3-methoxybenzyl)-propylamine, (4-hydroxy-3-methoxybenzyl)-isopropylamine and (4-hydroxy-3-methoxybenzyl)-butylamine. Any lower alkyl group of from 1 to 6 carbon atoms can be present and from economic consideration, methyl or ethyl are entirely satisfactory.

The hydrocyanic acid can be employed in an anhydrous form, or can be liberated in situ in the reaction mixture from alkali metal salts or alkaline earth metal cyanides in the presence of an acid, especially organic acids such as formic acid or acetic acid. An excess of acid is not detrimental.

Suitable solvents include water and all inert organic solvents, especially polar aprotic solvents such as N,N-dimethylformamide, dimethylsulfoxide, tetrahydrothiophene-S-dioxide, N-methyl-pyrrolidone, tetramethylurea and hexamethylphosphoric acid triamide. Of these, dimethylsulfoxide is used preferentially. In carrying out the reaction, preferably 1 to 1.5 mols of hydrocyanic acid, per mol of benzylamine, are employed. The temperature can vary from about 100° to about 190°C, preferably from about 110° to about 140°C. The reaction can be carried out under elevated pressure, but, preferably, normal pressure is used.

4-Hydroxy-3-methoxyphenylacetonitrile is a known intermediate for the preparation of the narcotic propanidid. Thus according to the known synthetic route, the nitrile is hydrolyzed to yield 3-methoxy-4-hydroxyphenylacetic acid which is esterfied to yield the corresponding propyl ester and finally etherified with N,N-diethylchloroacetamide to yield propyl-3-methoxy-4-(N,N-diethylcarbamylmethoxy)phenylacetate.

The following examples will serve to further typify the nature of this invention but should not be construed as a limitation on the scope thereof.

EXAMPLE 1

4-Hydroxy-3-methoxyphenylacetonitrile 160.8 g of N-methylvanillylamine and 54 g of sodium cyanide are suspended in 1 liter of dimethylsulphoxide and dissolved by heating to 125°C. At this temperature, a solution of 100 ml of glacial acetic acid in 200 ml of water is added and the mixture is stirred for a further 2 hours under nitrogen at 125°C. It then cooled to 80°C and the dimethylsulphoxide is distilled off in a water-pump vacuum. 900 ml of water are added to the residue which is extracted with 350 ml of chloroform. The chloroform phase is extracted by shaking with water and dried with sodium sulphate. On distilling off the chloroform in vacuo, an oil is obtained, which is cooled and seeded. The crystals formed melt at 53°–54°C (boiling point$_{0.1}$: 140°–144°C). The yield is 143 g (94% of theory).

EXAMPLE 2

160.8 g of N-methylvanillylamine are dissolved in 1,000 ml of dimethylsulphoxide and 32 g of anhydrous hydrocyanic acid are passed in at 125°C. The mixture is then stirred for 2 hours at 125°C. Working up takes place as indicated in Example 1. The yield is 132 g (87% of theory).

What is claimed is:
1. The process for the preparation of 3-methoxy-4-hydroxyphenylacetonitrile which comprises allowing an N-(lower alkyl)-3-methoxy-4-hydroxybenzylamine to react with hydrogen cyanide in a diluent at temperatures of from about 100°C to about 190°C.
2. The process according to claim 1 wherein the temperature is from about 110°C to about 140°C.
3. The process according to claim 1 wherein the hydrogen cyanide is generated in situ.
4. The process according to claim 1 wherein the diluent is water.
5. The process according to claim 1 wherein the diluent is an inert organic solvent.
6. The process according to claim 1 wherein N-methyl-3-methoxy-4-hydroxybenzylamine is employed.
7. The process according to claim 1 wherein N-methyl-3-methoxy-4-hydroxybenzylamine is allowed to react with hydrogen cyanide in an inert organic solvent at temperatures of from about 110°C to about 140°C.
8. The process according to claim 7 wherein the hydrogen cyanide is generated in situ from the reaction of an alkali metal cyanide and an acid.
9. The process according to claim 7 wherein the inert organic solvent is a polar aprotic solvent.
10. The process according to claim 9 wherein the solvent is dimethylsulfoxide.

* * * * *